United States Patent [19]

Hansen et al.

[11] 4,166,845

[45] * Sep. 4, 1979

[54] ANTIDANDRUFF SHAMPOO COMPOSITIONS CONTAINING AN AMINOPOLYUREYLENE RESIN

[75] Inventors: Kenneth R. Hansen, Staten Island, N.Y.; Paul S. Grand, South Bound Brook, N.J.

[73] Assignee: Colgate-Palmolive Company, New York, N.Y.

[ * ] Notice: The portion of the term of this patent subsequent to Nov. 19, 1991, has been disclaimed.

[21] Appl. No.: 795,356

[22] Filed: May 9, 1977

Related U.S. Application Data

[63] Continuation of Ser. No. 90,155, Nov. 16, 1970, abandoned.

[51] Int. Cl.$^2$ ............................................. A61K 31/785
[52] U.S. Cl. ....................................... 424/78; 252/106; 424/DIG. 2; 424/DIG. 4; 424/70
[58] Field of Search ................... 424/DIG. 4, 78, 70; 252/106

[56] References Cited

U.S. PATENT DOCUMENTS

| | | | |
|---|---|---|---|
| 2,963,465 | 12/1960 | van der Kerk | 260/77.5 |
| 2,973,342 | 2/1961 | Inaba et al. | 260/77.5 |
| 3,185,656 | 5/1965 | Gabler et al. | 260/30.2 |
| 3,390,137 | 6/1968 | Kirshenbaum et al. | 260/77.5 |
| 3,412,072 | 11/1968 | Bouboulis et al. | 260/77.5 |
| 3,580,853 | 5/1971 | Parran | 424/78 X |
| 3,849,548 | 11/1974 | Grand | 424/70 |

OTHER PUBLICATIONS

Kirk-Othmer, Encyclopedia of Chemical Technology, vol. 10, pp. 770–775 (1966), John Wiley & Sons, Inc., New York.

*Primary Examiner*—James O. Thomas, Jr.
*Assistant Examiner*—Vera C. Clarke
*Attorney, Agent, or Firm*—Richard N. Miller; Murray M. Grill; Herbert S. Sylvester

[57] ABSTRACT

This invention relates to a high-foaming antidandruff shampoo having desirable cosmetic conditioning properties, which consists essentially of about 10% to 30% by weight of a water-soluble betaine detergent, 1% to 10% by weight of a water-soluble anionic, amine oxide or amphoteric detergent, 1% to 10% by weight of a water-soluble nonionic detergent containing polyoxypropylene groups and polyoxyethylene groups, 0.5% to 5% by weight of an aminopolyureylene resin, and water.

10 Claims, No Drawings

ANTIDANDRUFF SHAMPOO COMPOSITIONS CONTAINING AN AMINOPOLYUREYLENE RESIN

This is a continuation, of application Ser. No. . . . 90,155 filed Nov. 16, 1970, now abandoned.

To achieve a complete shampoo, which for many years has been a goal of those who formulate shampoos, the product formulated must exhibit a unique combination of characteristics. It must have cleansing action in order to remove surface grease, dirt and skin debris which sloughs off from the hair shaft and scalp. It must lather well--producing copious, long-lasting foam during shampooing in both hard and soft water--yet the lather must be easily rinsed away. It must be effective in inhibiting dandruff, that is, the formation of visible masses of epidermal cellular debris which harbor the *Pityrosporum ovale* (*P. ovale*) groups of microorganisms. Further, it must function as a cosmetic conditioning agent by imparting luster, beauty, softness, and manageability to the hair. Finally, the physical character of the product should be such that it may be prepared in either a clear liquid Form or an opaque liquid form.

To date, the primary problem in formulating a shampoo with the above properties is that a particular ingredient will provide one or perhaps several of these properties but will adversely affect one or more of the other desirable properties. For example, soap shampoos exhibit satisfactory cleaning properties in soft water, but exhibit undesirable soap curds in hard water. On the other hand, the anionic detergent-based commercial shampoos clean so effectively that they leave the hair in an unmanageable condition, as evidenced by entanglement during wet and dry combing and by an electrostatic charge. To improve manageability, conditioning agents, such as lanolin and its derivatives, mineral oil, and polyglycols, have been added to shampoos to impart a conditioned state to the hair. However, these agents hinder lathering and leave a film on the hair which gives the hair an unpleasant, oily appearance. Alternatively, hair conditioning products may be applied to the hair after shampooing, but such applications are inconvenient and expensive.

Besides the shortcomings mentioned above, soap-based and synthetic detergent-based shampoos are not particularly effective in inhibiting formation of dandruff or visible skin debris. Therefore, it has been necessary to incorporate in the shampoo formulations special materials which have a particular effectiveness against visible skin debris. Generally, however, the more effective agents, such as zinc pyridinethione, selenium disulfide, sulfur, and 5,7-diiodo-8-hydroxyquinoline, are water-insoluble and, thus, tend to cause stability problems in the final product because of the tendency of the agent to separate or precipitate.

The compositions of the invention overcome the aforementioned shortcomings of the prior art compositions. More specifically, the inventive shampoo compositions are clear, homogeneous liquids which are characterized by their outstanding capacity to condition the hair cosmetically and to inhibit the growth of *P. ovale*, the yeast believed responsible for dandruff, and, at the same time, they possess the basic characteristics of commercially acceptable shampoos—clean but maintain hair luster, form copious, long-lasting lather in hard and soft water, and exhibit minimum refoaming action during rinsing. Thus, the inventive shampoos are the complete shampoos for which formulators have been diligently searching through the years.

In general, the complete shampoo compositions of the invention consist essentially of from 10% to 30% by weight of a betaine detergent, about 1% to 10% by weight of a water-soluble anionic, amine oxide or amphoteric detergent, about 1% to 10% by weight of a water-soluble nonionic detergent containing polyoxypropylene groups and polyoxyethylene groups about 0.5% to 5% by weight of an aminopolyureylene resin, and the balance water. Minor amounts of a $C_2$-$C_3$ monohydric alcohol or a $C_1$-$C_6$ lower alkylbenzene sulfonate may be included to improve its physical characteristics, such as its low temperature cloud point; and minor amounts of other ingredients, such as color and perfume, may be included for aesthetic reasons. The pH of the shampoo compositions varies from about 5.5 to about 10, and preferably from 7 to 9 for optimum performance and physical characteristics.

The essential detergent ingredient of the inventive shampoo compositions is a water-soluble betaine detergent having the formula $Z(N)R_1R_2CH_2CO_2$ wherein Z is an alkyl radical selected from the group consisting of $C_{10}$-$C_{16}$ alkyl, $C_{10}$-$C_{16}$ alkyl amidoethyl, and $C_{10}$-$C_{16}$ alkyl amidopropyl and $R_1$ and $R_2$ are each selected from the group consisting of $C_1$-$C_3$ alkyl and $C_1$-$C_3$ hydroxyalkyl. The alkyl and acyl radicals in Z may be obtained from natural sources, such as coconut oil, or from synthetic sources. For example, the alkyl and acyl groups obtained from coconut oil have the following composition: 3% $C_8$, 7% $C_{10}$, 48% $C_{12}$, 18% $C_{14}$, 9% $C_{16}$, and 10% $C_{18}$. The middle-cut, coconut-oil derived alkyl dimethyl betaine and the alkyl amidopropyl dimethyl betaine detergents are the preferred detergents.

The higher alkyl betaine detergents function as the primary foaming and cleaning agents in the described compositions. They are advantageous because they clean and cosmetically condition the hair simultaneously. Thus the shampooed hair is readily manageable in both the wet and the dry state. The concentration of betaine detergent will be about 10% to 30% by weight of the total composition, preferably about 14% to 25% by weight.

In addition to the primary betaine detergent, the shampoo composition will also include about 1% to 10% by weight, preferably 1% to 6% by weight, of a water-soluble supplementary detergent selected from the group consisting of anionic, amine oxide or amphoteric detergents. The latter detergent supplements the foaming and cleansing properties of the primary betaine detergent and has an advantageous cosmetic modifying effect on such properties as the static effects and the wet and dry feel of the hair. Generally, the supplementary detergent improves both the foam stability and the foam volume of the betaine detergent. Thus, the concentration of the supplementary detergent is related to the concentration of the primary detergent, and the weight ratios thereof range from about 1:1 to 1:7, preferably from 1:2 to 1:5.

Suitable supplementary detergents are the water-soluble alkyl sulfates, $R(OC_2H_4)_m OSO_3M$; trialkyl amine oxides, $R(R_1)_2N \rightarrow O$; acyl sarcosinates, $RCON(CH_3)CH_2CO_2M$; alkyl beta-aminopropionates, $RN(H)C_2H_4COOM$; alkyl beta-iminodipropionates, $RN(C_2H_4COOM)_2$; and the long-chain imidazole derivatives having the following formula.

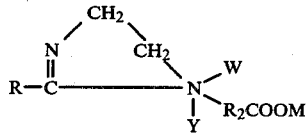

wherein R is an acyclic group of from 10 to 18 carbon atoms; m is 0 to 5; $R_1$ is $C_1$–$C_3$ alkyl or $C_1$–$C_3$ hydroxyalkyl; W is selected from the group of $R_2OH$, $R_2COOM$, and $R_2OR_2COOM$; $R_2$ is an alkylene or hydroxyalkylene group containing 1 to 4 carbon atoms; Y is selected from the group consisting of $OH^-$, $R_3OSO_3$—; $R_3$ is selected from the group consisting of alkyl, alkyl aryl, and fatty acyl glyceride groups having 6 to 18 carbon atoms in the alkyl or acyl group; and M is a water-soluble cation, e.g., sodium, potassium, ammonium, or mono, di, and triethanolammonium. Imidazole detergents are described in U.S. Pat. Nos. 2,773,069, 2,781,354, and 2,781,357. The acyclic group may be derived from natural sources, such as coconut oil, or synthetic sources and preferably is a hydrocarbon alkyl or alkylene group.

Other suitable supplementary detergents are the N-(2-hydroxy $C_{10}$–$C_{18}$ alkyl) derivatives of N-methyl taurinaate, sarcosinate, N-methyl taurinate-N-oxide, sarcosinate-N-oxide, and diethanolamine. These detergents correspond to the following formula: $R_4X$ wherein $R_4$ is a 2-hydroxy alkyl group containing 10 to 18 carbon atoms and X is selected from the group consisting of $N(CH_3)CH_2CH_2SO_3M$,

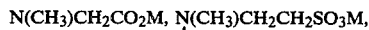
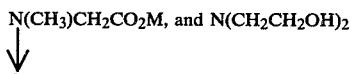

wherein
M is selected from the group consisting of sodium potassium, ammonium and mono di and triethanolammonium. Such detergents are disclosed in the co-pending application of Kenneth R. Hansen entitled "Liquid Detergent Compositions" filed of even date herewith.

The N-(2-hydroxy higher alkyl) N-methyl taurinates have the formula $RCH(OH)CH_2N(CH_3)CH_2CH_2SO_3M$ and may be prepared by simple addition of N-methyl taurine salt to a 1,2 epoxyalkane containing about 10 to 18 carbon atoms. The addition technique produces an N-(2-hydroxyalkyl) N-methyltaurine salt which is relatively free from inorganic impurities. The epoxide raw material is made by conventional oxidation of compounds derived from petroleum. The N-oxide derivatives of the N-(2-hydroxyalkyl) N-methyl taurinates may be prepared by oxidizing the corresponding N(2-hydroxyalkyl) N-methyl taurinate with hydrogen peroxide or ozone to convert the amine to an amine oxide. The N-(2-hydroxyalkyl) sarcosinates, $RCH(OH)CH_2N(CH_3)CH_2CO_2M$, and their N-oxides may be prepared in the same manner as the taurinate derivatives. The N-(2-hydroxyalkyl) diethanolamine is similarly prepared by adding diethanolamine to the desired 1,2-epoxyalkane.

Amounts of 1% to 10%, preferably 2% to 8%, by weight of a water-soluble nonionic detergent containing polyoxypropylene groups and polyoxyethylene groups in the molecule are generally included in the shampoo compositions to modify the feel of the foam and to promote rinsing by minimizing the tendency of the detergents to foam again. The water-soluble block copolymers formed by condensing ethylene oxide with a hydrophobic base formed by the condensation of propylene oxide with propylene glycol and sold under the trade name "Pluronic" are suitable. The molecular weight of the block copolymers varies from about 1,300 to 15,000 with the weight of the hydrophobe being from about 1,200 to 3,500 and the ethylene oxide content being about 10% to 80% by weight. "Pluronic L-62" having a hydrophobe molecular weight of 1,750 and containing 20% by weight of ethylene oxide is a preferred nonionic detergent. Other suitable nonionics are the polyoxyethylene polyoxypropylene adducts of $C_1$–$C_8$ alkanols described in U.S. Pat. No. 2,425,755 which are sold under the trade name "Ucon". These nonionics have a molecular weight in the range of about 600 to 4000 and consist of a heteric chain of oxyethylene and oxypropylene condensed on a $C_1$–$C_8$ alkanol. The weight ratio of oxyethylene to oxypropylene varies from about 3:1 to 1:3. A preferred nonionic detergent of this type is "Ucon 50HB 5100," which has a molecular weight of about 4000 and is the condensation product of a mixture of 50% ethylene oxide and 50% propylene oxide on butanol. Mixtures of the nonionic detergents may also be used.

The amino polyureylene (APU) resins are primarily employed in the shampoo compositions because of their antimicrobial effectiveness against P. ovale, the yeast found in the visible skin debris or dandruff. In addition, however, the APU resins significantly improve the foam stability as evidenced by an increase in foam drainage time of the primary betaine detergent and in combination with the supplementary detergent achieve desirable cosmetic conditioning of the hair. Further, the APU resins are soluble in the shampoo compositions so that either clear or opaque shampoo compositions may be prepared wherein separation of the antidandruff agent is not a problem. Such resins are generally present in an amount of about 0.5% to 5% by weight of the shampoo with optimum cosmetic-antidandruff effects being noted in the range of 1% to 3%.

APU resins suitable for use in the described compositions are water-soluble polymeric resins characterized by the following repeating unit:

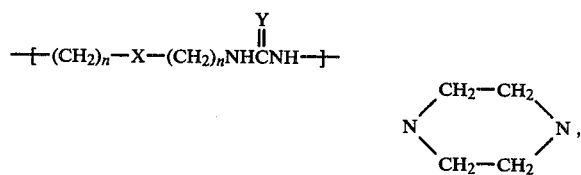

wherein X is NH, N—$C_1$ to $C_{22}$ alkyl,

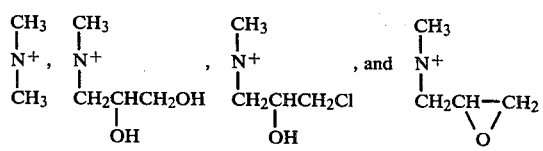

Y is O or S, and n is 2 or 3.

Such APU resins and their bacterial effectiveness are set forth in the copending application of Paul Grand entitled "Cosmetic Compositions" filed of even date herewith. Thus, suitable APU resins include both the polyurea- and the polythiourea-containing compounds. Preferred APU resins have a repeating unit where Y is oxygen, n is 3, and X is selected from the group consisting of N—$C_{1-8}$ alkyl and

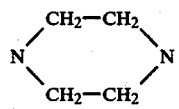

Generally, the number of repeating units in the resin will be sufficient to yield a polymer having a molecular weight in the range of about 300 to 100,000. Preferred APU resins have an average molecular weight in the range of 1,000 to 20,000 and a particularly preferred resin is the reaction product of equimolar quantities of N-methyl, bis(3-aminopropyl) amine and urea having a molecular weight of about 4,300.

The molecular weight of the APU resin is based upon aqueous gel permeation chromatographic analysis. The separation is carried out in oxalic acid solution, adjusted to pH 3.5 on three Corning controlled-pore glass columns (nominal pore sizes 175), 125, and 75 Å) in series. Detection is by differential refractometer. Reference compounds are dextran polysaccharides of molecular weights of 150,000, 110,000, 40,000, 20,000, and 10,000 and sucrose and galactose.

The APU resins which can be used in the compositions of this invention are prepared by reacting, for example, 145 grams of N-methyl bis(3-aminopropyl) amine (1.0 mole) and 60 grams of urea (1.0 mole) in a 3-necked flask equipped with a thermometer, mechanical stirrer, condenser, and nitrogen sparge tube. Nitrogen is bubbled slowly through the solution throughout the course of the reaction. The solution is heated to 140° C. over a 20-minute interval where ammonia begins to evolve. The solution is further heated to 250° C. over a 30 minute interval and allowed to cool. The product is a hard, resinous powder (Resin A) having a molecular weight of about 4300. The secondary amine analogues can be made by the above process if bis (3-aminopropyl) amine or bis (2-aminoethyl) amine are reacted with urea or thiourea. The piperazine analogues are made by reacting N,N'-di(3-aminopropyl) piperazine on N,N'-di(2-aminoethyl) piperazine with urea or thiourea. The N—$C_1$ to $C_{22}$ alkyl analogues are prepared by reacting N—$C_1$ to $C_{22}$ alkyl bis(3-aminopropyl) amine or N—$C_1$ to $C_{22}$ alkyl bis (2-aminoethyl) amine with urea or thiourea. Additional analogues are prepared by the following reactions:

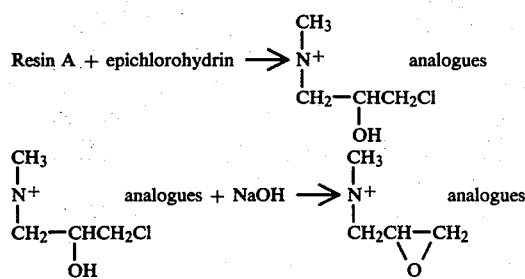

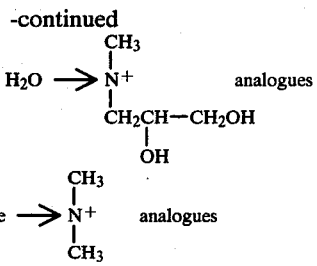

The preparation of the remaining analogues is well within the skill of the art following the above techniques.

The balance of the composition generally consists of water in a concentration of about 45% to 87.5% by weight of the shampoo, preferably from 65% to 75%. Where necessary for clarity or for a reduction in the lower-temperature cloud point, from 1% to 15% by weight of a $C_2$–$C_3$ monohydric alcohol, such as ethanol or isopropanol, may be included in the shampoo compositions. Alternatively, water-soluble $C_1$–$C_6$ lower alkyl benzene sulfonate salts, such as sodium and potassium, may be included in amounts of from 0.3% to 4% by weight of the shampoo as cloud-point depressant.

Optionally, from about 0.2% to about 2.0% by weight of a water-soluble subresinous to resinous condensation product having a molecular weight of 500 to 100,000 or higher, preferably from 20,000 to 80,000 of a polyalkylene polyamine with a polyfunctional aliphatic dihalide or halohydrin may be included to modify the slip or feel of the foam. Examples of polyfunctional aliphatic compounds are ethylene dichloride, alphadichlorohydrin, dibromohydrin, di-iodohydrin, epichlorohydrin, epibromohydrin, epiidohydrin, diepi-iodohydrin. The alkylene polyamines correspond to the formula $H_2N(C_nH_{2n}HN)_xH$ in which x is 1 to 5 and n is 2 to 4 and include ethylenediamine, 1,3-propylene diamine, diethylenetriamine, triethylenetetraamine, tetraethylenepentamine, and the corresponding polypropylenepolyamines and polybutylenepolyamines. Such products are well known as disclosed in U.S. Pat. No. 2,765,228. A preferred resin is the water-soluble condensation product of diethylenetriamine (1 mole) with 1 to 3 moles of epichlorohydrin having a molecular weight of about 80,000.

Additional ingredients may be incorporated into the instant shampoos. Such ingredients include minor proportions of perfumes and colors for aesthetic purposes, lanolin, sequestering agents, such as citrate and ethylenediamine tetraacetate, and opacifiers, such as zinc stearate and magnesium stearate.

Specific inventive shampoo compositions are illustrated by the following examples. All quantities indicated are by weight unless otherwise indicated.

EXAMPLE 1

A hair-shampoo formulation having the following composition is prepared.

| | Percent |
| --- | --- |
| $C_{10}$–$C_{16}$ alkyl* amidopropyl dimethyl betaine | 16.0 |
| Triethanolamine lauryl sulfate | 4.0 |
| Lauryl dimethyl amine oxide | 0.5 |
| Polyoxypropylene-polyoxyethylene block copolymer having a hydrophobic molecular weight of 1,750 and containing 20% by weight of polyoxyethylene | 5.0 |

-continued

| | Percent |
|---|---|
| Condensation product of a 1:1 mixture of ethylene oxide and propylene oxide on butanol (m.w. = 4000) | 2.0 |
| Resinous condensate of about 2 moles of epichlorohydrin and one mole of diethylenetriamine having a molecular weight of about 80,000 | 0.5 |
| Resin A | 2.0 |
| Ethanol | 1.9 |
| Water | balance |
| | 100.0 |

*Alkyl group corresponds to the mixture of alkyls obtained from a middle-cut of coconut oil, e.g., 1% $C_{10}$, 65% $C_{12}$, 27% $C_{14}$, and 7% $C_{16}$.

The foregoing composition is prepared by admixing the surfactant ingredients with the formula weight of water with agitation at a temperature in the range of 130° F. to 160° F. Resin A and the resinous condensate ingredients are added to the aqueous surfactant mixture with agitation at a temperature in the range of 45° F. to 160° F. After homogeneity is attained, the mixture is cooled to 80° F.–90° F. with agitation and the pH is adjusted, if necessary, by adding either sulfuric, hydrochloric or citric acid or triethanolamine, sodium hydroxide or potassium hydroxide. The resultant product is a clear liquid at pH 7.5 and has a cloud point below 32° F. The shampoo exhibits outstanding cleaning, foaming, and hair-conditioning properties in normal shampooing operations.

The outstanding foaming characteristics of the shampoo of Example 1 in the presence of sebum soil are illustrated in the following test. Twenty-five grams of shampoo solution are diluted to one hundred milliliters with water containing 250 parts per million of hardness (160 ppm. of $Ca^{++}$ and 90 ppm. of $Mg^{++}$) in the presence of three grams of Synthetic sebum soil, and the temperature of the mixture is adjusted to 100° F. The one hundred milliliters of solution is then transferred to a five hundred milliliter graduated cylinder (total volume capacity of over 600 ml. of water) containing a water-filled plastic cylinder (17 millimeter diameter, 72 millimeter height, and a displacement volume equal to twenty-five milliliters of water), and the five hundred milliliter cylinder is affixed to a mechanical rotator assembly where it is rotated through twenty complete cycles or revolutions to generate foam. Rotations are completed within thirty-five to fifty-five seconds. The foam volume is noted at the conclusion of the rotations, and the time interval in seconds from the completion of the rotations to the point at which seventy-five milliliters of liquid have been drained is recorded as the drainage time. The values for the composition of Example 1 are 650 cubic centimeters (cc.) of total foam and 300 seconds foam-drainage time. Comparable figures for high-foaming, high performing, commercial shampoos based on alkyl sulfate detergent are 475 c.c. foam volume and 139 seconds foam drainage time.

Resin A has a beneficial effect upon foam volume and foam stability because comparable figures for a composition not containing APU resin are 450 c.c. of foam and 110 seconds foam drainage time.

When the antimicrobial effectiveness of the foregoing composition against *P. ovale* is determined using the "Test Tube Serial Dilution Method" described at pages 195–200 of the Fifth Edition of "Diagnostic Bacteriology" by Schaub et al., the composition exhibits a "minimum inhibitory concentration" (MIC) of 98 micrograms per milliliter (μg/ml.) based on the weight of shampoo or 1.95 μg/ml. based upon the weight of the APU resin. Further, when the composition is formulated with a radioactive $C_{14}$ tagged Resin A and checked for protein substantivity, a value of 414 μg./disk is noted. (Substantivity is determined by stirring a half-inch diameter circular gelatin disk weighing 42 milligrams for 15 minutes in ten grams of a 25% weight concentration of shampoo containing radioactive (C-14 tagged) APU Resin A, rinsing the disk five times in ten milliliters of water, and measuring the radiation emission with the aid of a thin window gas flow Geiger-Muller counter.

The antidandruff properties of the shampoo composition were determined in clinical testing wherein the composition of Example 1 was compared with a 17% by weight triethanolamine myristate placebo shampoo composition known to be ineffective against dandruff and a commercial antidandruff shampoo containing zinc pyridinethione as the antidandruff ingredient. In the clinical test, a skilled evaluator determined dandruff rating for each of the subjects before beginning testing, once a week during the two weeks on the placebo shampoo (to establish a baseline), and once a week during the six weeks on the test shampoo. (For one third of the group, the placebo shampoo was the test shampoo.) During the six week test period, each subject washed his hair with 18 c.c. of shampoo using one half of the shampoo in two consecutive washings, had his dandruff rating determined on the seventh day, and shampooed again after the rating. Between shampooings, each subject used only a specified hairdressing having minimum effect on dandruff scores daily. The test results indicated that the composition of Example 1 was effective in reducing dandruff, and its effectiveness was equivalent to that of the commercial shampoo containing zinc pyridinethione.

During testing, the cosmetic conditioning characteristics of the composition of Example 1 were evaluated against commercial shampoo formulations by skilled beauty operators using the well known "half head" technique. The composition of the example showed a marked advantage in ease of wet and dry combing, and was equivalent in curl-retention and static-charge reduction.

EXAMPLES 2 AND 3

The composition of Example 1 is repeated with the exception that the concentration of triethanolamine lauryl sulfate (TEALS) is reduced from 4% by weight to 2% and 1% by weight. The resultant products are clear, homogeneous shampoos having cosmetic conditioning properties comparable to those of Example 1. The foaming characteristics in the presence of sebum soil are determined using the method outlined in Example 1 with the following results.

Table I

| Example | | Foam Volume (C.C.) | Drainage Time (sec.) |
|---|---|---|---|
| 2 | 2% TEALS | 650 | 154 |
| 3 | 1% TEALS | 550 | 138 |

These results show that a reduction in the supplementary detergent, TEALS, may result in a reduction in both foam volume and foam stability.

EXAMPLES 4-6

The composition of Example 1 is repeated with the exception that 4% by weight of the disodium salt of 2 undecyl,1-ethoxyethanoic acid, 1 ethanoic acid, 1-lauryl sulfate imidazoline sold as "Miranol 2 MCA," sodium N-lauryl sarcosinate, and a mixture of sodium N-lauryl myristyl-aminopropionate (9 parts) and disodium N-lauryl myristyl iminodipropionate (1 part) sold as "Deriphat 170C" respectively is substituted for the 4% of the triethanolamine sulfate detergent. Foaming results using the test method in Example 1 are tabulated in Table III.

Table II

| Example | Detergent | Foam Volume (cc.) | Foam Stability (cc.) |
|---|---|---|---|
| 4 | "Miranol 2MCA" | 600 | 157 |
| 5 | Sodium N-lauroyl sarcosinate | 650 | 150 |
| 6 | "Deriphat 170" | 650 | 98 |

The resultant shampoos have satisfactory foaming properties and exhibit cosmetic conditioning properties when used in shampooing. Antimicrobial effects against *P. ovale* are comparable to those of Example 1.

When sodium N(2-hydroxyhexadecyl) N-methyl taurinate or sarcosinate or their N-oxides are substituted for triethanolamine sulfate detergent in the composition of Example 1, satisfactory "complete" shampoos are also achieved.

EXAMPLE 7

A shampoo having the following composition is prepared.

|  | Percent |
|---|---|
| Coconut alkyl amidopropyl dimethyl betaine* | 16.0 |
| Triethanolamine lauryl sulfate | 1.0 |
| "Pluronic L-62" | 5.0 |
| Analogue of Resin A having repeating unit $+(CH_2)_3N^+(CH_3)_2(CH_2)_3NHC(O)NH+$ a molecular weight of about 4600 | 1.0 |
| Water | balance |
|  | 100.0 |

The resultant antidandruff shampoo is a clear liquid which exhibits good foaming and conditioning properties when used in shampooing.

When resins having an average molecular weight in the range of 1000 to 20,000 and a repeating unit of $+(CH_2)_3N^+(CH_3)(CH_2CHCH_2OH)(CH_2)_3NH\ C(O)NH+$ or
 $\quad\quad\quad\quad\quad\quad |$
 $\quad\quad\quad\quad\quad\quad OH$ $+(CH_2)_3N^+(CH_3)(CH_2CHCH_2Cl)(CH_2)_3NH\ C(O)NH+$ or
 $\quad\quad\quad\quad\quad\quad |$
 $\quad\quad\quad\quad\quad\quad OH$

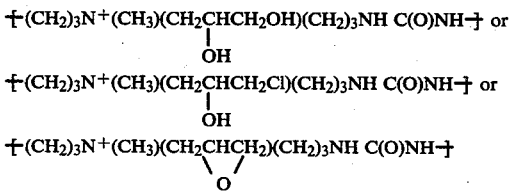

are substituted for the resin in the composition of example 7, substantially similar results are obtained.

EXAMPLE 8

The composition of Example 1 is repeated but 1% by weight of the N,N'-di(3-aminopropyl) piperazine urea resin having a molecular weight of about 5600 is substituted for Resin A. The resultant clear liquid shampoo exhibits antimicrobial effectiveness against *P. ovale* and good conditioning effects as evidenced by low static and easy wet and dry combing.

EXAMPLE 9

The following clear antidandruff shampoo composition is prepared.

|  | Weight percent |
|---|---|
| Coconut alkyl amidopropyl dimethyl betaine* | 22.5 |
| Sodium N-(2-hydroxy hexadecyl) N-methyl taurinate | 6.0 |
| Sodium hexyl benzene sulfonate | 0.8 |
| $C_{12}$-$C_{16}$ alkyl dimethyl amine oxide | 0.6 |
| Polyoxypropylene - polyoxyethylene block copolymer (hydrophobe molecular weight of 1750 and 20% by weight of polyoxyethylene) | 5.0 |
| Resin A | 2.0 |
| Water | balance |
|  | 100.0 |

*Alkyl mixture derived from middle-cut of coconut oil

Similar results may be obtained when the quaternized analogues of Resin A containing $N^+(CH_3)(CH_2CHCH_2Cl)$ or
 $\quad\quad\quad |$
 $\quad\quad\quad OH$

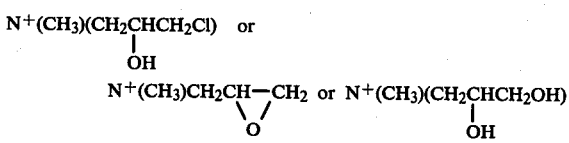

in the repeating group are substituted for Resin A in the composition of Example 9.

EXAMPLE 10

A satisfactory shampoo having the following composition is prepared.

|  | % By Weight |
|---|---|
| Coco-dimethyl amidopropyl glycine | 16.0 |
| Lauryl bishydroxyethyl amine oxide | 4.0 |
| Condensation product of 1:1 mixture of ethylene oxide and propylene oxide on butanol (M.W. = 4000) | 2.0 |
| Polyoxypropylene-polyoxyethylene block copolymer having a hydrophobic molecular weight of 1750 and containing 20% by weight of polyoxyethylene | 5.0 |
| Quaternary ammonium substituted cellulose ether polymer obtained from Union Carbide under the name "JR-IL"[a] | 2.5 |
| Resin A | 2.0 |
| Ethanol | 1.9 |
| Water | balance |
|  | 100.0 |

[a] Molecular weight in range of 100,000 to 1,000,000

The pH of the foregoing shampoo is adjusted to 7.5 with 10% hydrochloric acid solution. This shampoo exhibits good foam volume and high foam stability when tested using the procedure used with Example 1.

Substitution of lauryl dimethyl amine oxide for the lauryl bishydroxyethyl amine oxide in Example 10 yields a shampoo having similar foaming and cosmetic properties.

Although the present invention has been described with reference to particular embodiments and examples, it will be apparent to those skilled in the art that variations and modifications of this invention can be made and that equivalents can be substituted therefor without departing from the principles and spirit of the invention.

What is claimed is:

1. A high-foaming, antidandruff shampoo having cosmetic conditioning properties consisting essentially of about 14% to 25% by weight of a water-soluble betaine detergent having the formula $Z(N)R_1R_2CH_2CO_2$ wherein Z is a radical selected from the group consisting of $C_{10}-C_{16}$ alkyl, $C_{10}-C_{16}$ alkyl amidoethyl, and $C_{10}-C_{16}$ alkyl amidopropyl, and $R_1$ and $R_2$ are selected from the group consisting of $C_1-C_3$ alkyl and $C_1-C_3$ hydroxyalkyl; 1% to 6% by weight of a water-soluble supplementary detergent selected from the group consisting of alkyl sulfate, $R(OC_2H_4)_mOSO_3M$, trialkyl amine oxide, $R(R_1)_2N \rightarrow O$, acyl sarcosinate $RC(O)N(CH_3)CH_2CO_2M$, alkyl beta-aminopropionate, $RN(H)C_2H_4CO_2M$, alkyl beta-iminodipropionate, $RN(C_2H_4CO_2M)_2$, imidazole derivative,

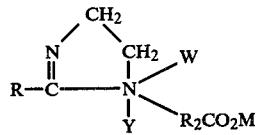

and 2-hydroxyalkyl detergent, $R_4X$, wherein R is an alkyl group of 10 to 18 carbon atoms, m is 0–5, $R_1$ is selected from the group consisting of $C_1-C_3$ alkyl and $C_1-C_3$ hydroxyalkyl, W is selected from the group consisting of $R_2OH$, $R_2CO_2M$, and $R_2OR_2CO_2M$, $R_2$ is an alkylene group or hydroxyalkylene group of 1 to 4 carbons, Y is selected from the group consisting of $OH^-$ and $R_3OSO_3$ and $R_3$ is selected from the group consisting of alkyl, alkyl aryl and fatty acyl glyceride groups having 6 to 18 carbons in the alkyl or acyl group, $R_4$ is a 2-hydroxy-alkyl group containing 10 to 18 carbons, X is selected from the group consisting of

$N(CH_3)CH_2CO_2M$, and $N(CH_2CH_2OH)_2$, and M is a cation selected from the group consisting of sodium, potassium, ammonium, and mono-, di-, and triethanolammonium; 2% to 8% by weight of a water-soluble nonionic detergent selected from the group consisting of a block copolymer of ethylene oxide and propylene oxide on propylene glycol wherein ethylene oxide is 10% to 80% by weight and the molecular weight of the hydrophobe is about 1,200 to 3,500 and a condensate of a heteric mixture of oxypropylene and oxyethylene in a ratio of 3:1 to 1:3 on a $C_1-C_8$ alkanol, said condensate having a molecular weight in the range of 600 to 4,000 and mixtures thereof; 1% to 3% of an aminopolyurey-lene resin having a molecular weight in the range of 300 to 100,000 and characterized by the following repeating unit

where X is NH, N-$C_1-C_{22}$ alkyl, or

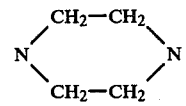

and n is 2 or 3; and water.

2. A shampoo as set forth in claim 1 which contains in addition from 0.3% to 2% by weight of a resinous condensation product of an alkylene polyamine of the formula $H_2N(C_nH_{2n}NH)_xH$ in which x is 1 to 5 and n is 2 to 4 and ethylene dichloride or a halohydrin, said condensate having a molecular weight of 500 to 100,000.

3. A shampoo as set forth in claim 1 wherein said repeating unit is

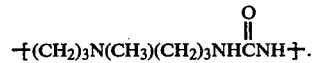

4. A shampoo as set forth in claim 1 which contains in addition from 1% to 15% by weight of a $C_2-C_3$ monohydric alcohol.

5. A shampoo as set forth in claim 1 wherein said betaine is $C_{10}-C_{16}$ alkyl amidopropyl dimethyl betaine, said supplementary detergent is selected from the group consisting of said alkyl sulfate, said trialkyl amine oxide and said alkyl beta-aminopropionate and said nonionic detergent is said block copolymer.

6. A shampoo as set forth in claim 5 wherein said supplementary detergent is triethanolamine alkyl sulfate.

7. A shampoo as set forth in claim 5 wherein said repeating unit of the resin is $+(CH_2)_3N(CH_3)(CH_2)_3NHC(O)NH+$.

8. A shampoo as set forth in claim 5 wherein said supplementary detergent is said trialkyl amine oxide.

9. A shampoo as set forth in claim 5 wherein said supplementary detergent is said alkyl beta-aminopropionate salt.

10. A shampoo as set forth in claim 5 wherein said nonionic detergent is a mixture of said block copolymer and the condensate of a heteric mixture of oxypropylene and oxyethylene in a ratio of 3:1 to 1:3 on a $C_1-C_8$ alkanol, said condensate having a molecular weight in the range of 600 to 4000.

* * * * *